United States Patent [19]

Hill

[11] 4,387,784

[45] Jun. 14, 1983

[54] STETHOSCOPE WITH IMPROVED RESONANT CAVITY AMPLIFICATION

[76] Inventor: Raymond R. Hill, 310 Diogenes Dr., Angwin, Calif. 94508

[21] Appl. No.: 309,030

[22] Filed: Oct. 6, 1981

[51] Int. Cl.³ .......................... A61B 7/02; H04R 25/00
[52] U.S. Cl. ..................................... 181/131; 181/137
[58] Field of Search ............... 181/131, 132, 135, 137; 179/1 SK

[56] References Cited

U.S. PATENT DOCUMENTS

| | | | |
|---|---|---|---|
| 2,389,868 | 11/1945 | Olson | 181/131 |
| 3,185,251 | 5/1965 | Dudler | 181/137 |
| 3,314,499 | 4/1967 | Blackman | 181/131 |
| 4,270,627 | 6/1981 | Hill | 181/131 |

Primary Examiner—Benjamin R. Fuller
Attorney, Agent, or Firm—Majestic, Gallagher, Parsons & Siebert

[57] ABSTRACT

One or more resonant cavities are selectively connected to the main sound passage of a stethoscope in order to selectively amplify frequency ranges of interest. The amplified frequency range is controlled by positioning a vent in a side wall of the resonant cavity a particular distance from the pick-up head. An improved sound pick-up head probe structure is rugged and allows extending the length of the probe when desired.

14 Claims, 7 Drawing Figures

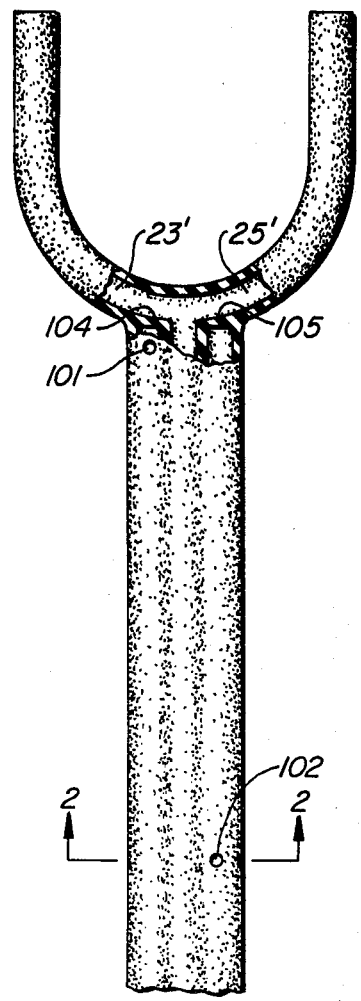
FIG._1.
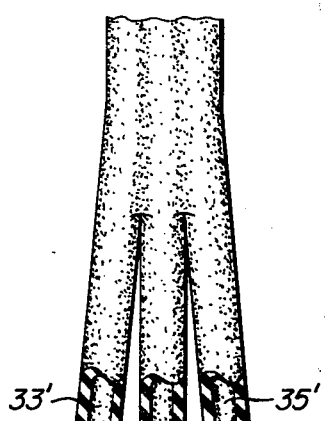
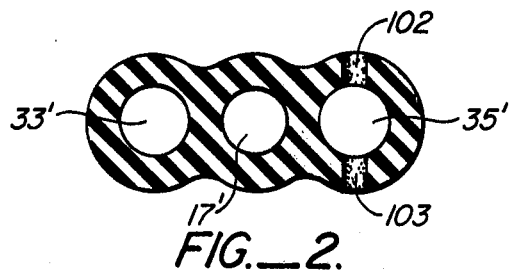
FIG._2.
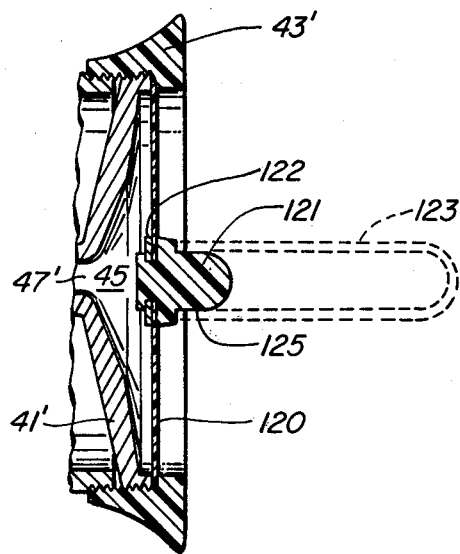
FIG._5.
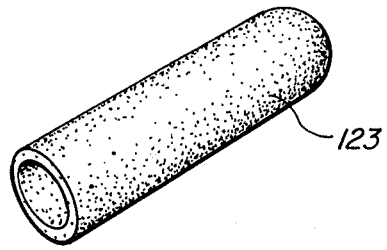
FIG._5A.

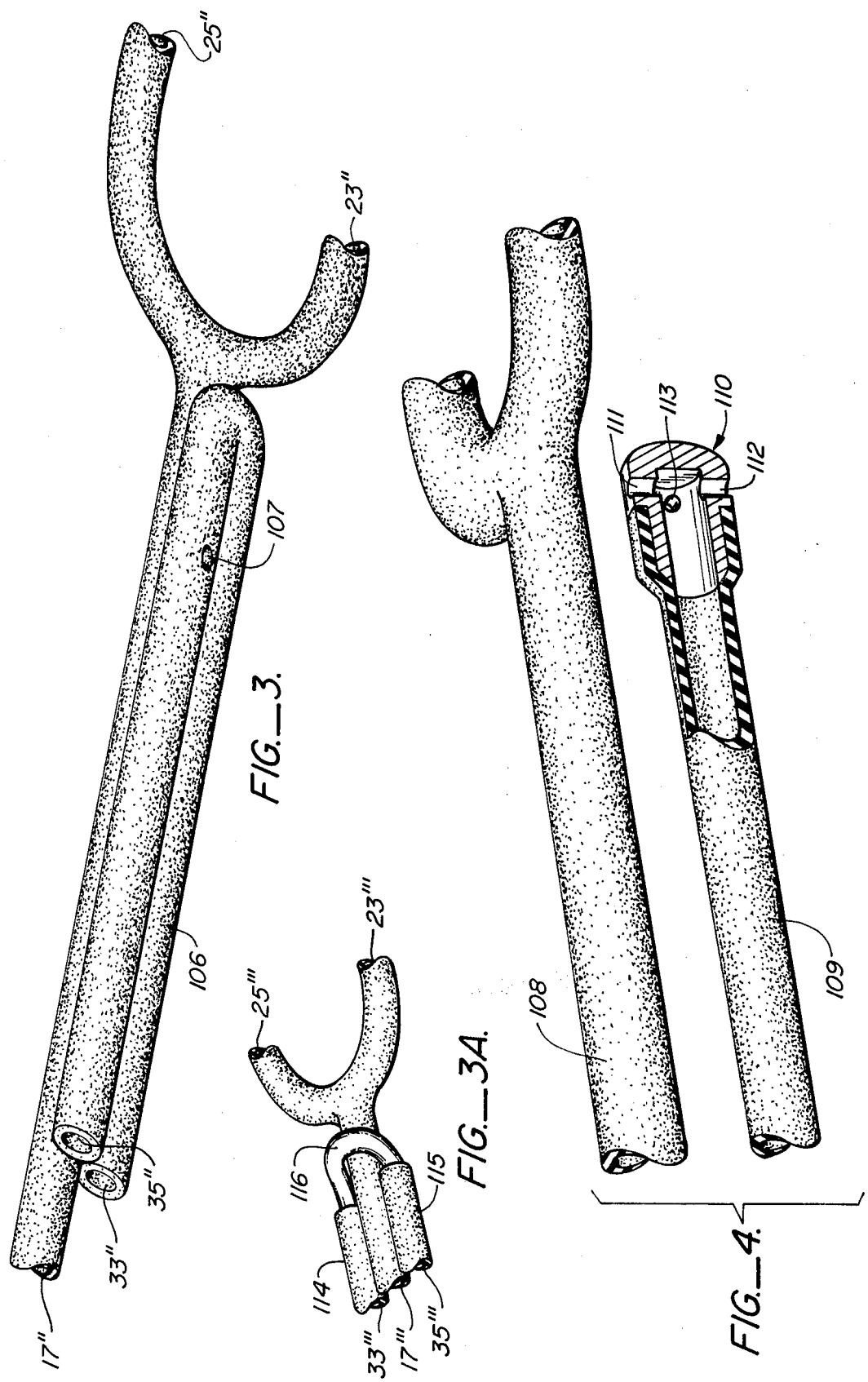

STETHOSCOPE WITH IMPROVED RESONANT CAVITY AMPLIFICATION

CROSS-REFERENCE TO A RELATED PATENT

This application is related to U.S. Pat. No. 4,270,627, which issued June 2, 1981, the entire contents of which are expressly incorporated herein by reference, and is referred to hereinafter as the "prior patent".

BACKGROUND OF THE INVENTION

The prior patent describes an extremely advantageous technique for mechanically amplifying sounds within a frequency range of interest in a stethoscope, wherein a resonant cavity is connected to the stethoscope's sound passage. The resonant cavity is vented to the atmosphere, most conveniently in the form of a flexible tube having its end completely opened. The length of the tube from the pick-up head to the vent determines the frequency range of its amplification. Two, or even more, resonant cavities of different lengths can be utilized along with a manual control valve connecting them to the sound passage, so that the frequency range of amplification may be selected by the user of the stethoscope for listening to different functions of a patient's heart and lungs.

It is a primary object of the present invention to further improve the characteristics of such resonant cavity sound amplification in stethoscopes.

It is also an object of this invention to provide an improved sound pick-up head construction.

SUMMARY OF THE INVENTION

These and additional objects are accomplished by the present invention, wherein, briefly, according to one aspect, the resonant cavities or tubes are vented to the atmosphere through holes in their sides, the distance from the sound pick-up to such a hole determining the frequency range that is amplified by the chamber. It has been found that so long as the vents are of sufficient size with respect to the cross-sectional area of the internal cavity, that whatever occurs in the tube beyond that point has practically no effect on the resonant chamber amplification characteristics. A preferred range of the vent area is within substantially one-half to two times the cross-sectional area of the tube at the point where it is vented through the sides.

The side venting has an advantage of making it easy to form a resonant cavity of a particular frequency response. A supply of cavities or tubes of uniform dimensions may be provided with vents conveniently positioned in them at a later time to give the desired individual characteristics.

A further advantage is an isolation of the resonant cavity from a noisy atmosphere that may surround the stethoscope when used. A side vent accomplishes this if the cavity is otherwise enclosed; that is, when the cavity forming tube is closed off except for the vent. To maximize this advantage, the vents are formed by two or more opposing apertures in the side walls a given distance from a pick-up head.

According to another aspect of the present invention, a sound pick-up head is formed with a solid patient contacting probe piece attached to a flat diaphragm. This provides a non-breakable, rugged pick-up head. An extension is easily attached to the probe so that the stethescope can be more easily used with small laboratory animals.

Additional objects, advantages and features of the present invention will become apparent from the following detailed description of its preferred embodiment, which description should be taken in conjunction with the accompanying drawings.

BRIEF DESCRIPTION OF THE DRAWINGS

FIG. 1 shows a specific example of the stethoscope piece that utilizes the present invention;

FIG. 2 is a cross-sectional view of the piece of FIG. 1 taken at section 2—2 thereof;

FIGS. 3 and 3A show other specific examples utilizing the improved techniques of the present invention;

FIG. 4 shows yet a further example of a stethoscope using the techniques of the present invention; and FIGS. 5 and 5A show an improved sound pick-up head probe assembly.

DESCRIPTION OF THE PREFERRED EMBODIMENTS

FIG. 1 shows an example of a flexible sound transmission tube assembly for use in the stethoscope between a sound pick-up head (not shown) and ear pieces (not shown). This is adapted, according to this example, to replace the tube assembly between the pick-up head 11 and the ear piece assembly 19, 21, 27, 29 and 31 of the stethoscope embodiment shown in FIGS. 1, 2, 3A, 3B and 3C of the prior patent. The portions of the assembly of FIG. 1 that serve the same function as portions of the FIGS. 1-3 embodiment of the prior patent are identified with the same reference number but with a prime (') added. A main sound transmission passage 17' and resonant cavities 33' and 35' are formed independent of one another by three adjacent tubes that are adapted to be connected to the sound pick-up head 11 of the prior patent in the same way as its corresponding tubes. The main sound transmission passage 17' is split at a Y at its other end into passages 23' and 25' for attachment to individual ear pieces.

Rather than being open at their ends opposite to the connection with the sound pick-up head 11, the resonant cavities 23' and 35' are completely enclosed except for vents to the atomosphere provided in their side walls at particular distinct distances from their ends that are adapted for connection to the sound pick-up head 11 of the prior patent. An aperture 101 is provided through the tube into the chamber 33', and a similar aperture (not shown) is formed on the opposite side of the chamber from the aperture 101. Similarly, a pair of opposing apertures 102 and 103 vent the chamber 35' to the atmosphere and are positioned at a shorter distance from the sound pick-up head than is the vent 101. This results in the chamber 35' amplifying a range of sound at a higher frequency while chamber 35' amplifies lower frequency sounds.

It has been found that there is substantially no effect on the sound amplifying characteristics of such a resonant chamber by the structure of that chamber on the opposite side of its vents from the sound pick-up head. The tube chamber ends remote from the pick-up head can be opened to the atmosphere or closed without affecting the range of frequencies that is amplied by that chamber when connected to the main sound transmission passage 17'. This range of frequencies and the amplification characteristic of that range appear to be established by the distance of the vent from the sound pick-up head. This assumes that the vent is large enough for the amplification desired, and the total area of the opposing apertures forming each of the vents in the FIG. 1 embodiment are preferably in excess of 50% of the cross-sectional area of the resonant cavity at the location of those apertures. The use of the side vents has a significant advantage in the flexibility it gives in the design of a stethoscope and the ease of packaging the resonant chambers as an integral part of the instrument.

Another important advantage of side vents is the ability to significantly reduce the effect of surrounding room sounds from interfering with the stethoscope user's monitoring of patient sounds. Although the resonant tube structures of the prior patent still represent a significant improvement over prior techniques, the use of side vents as shown with respect to FIG. 1 herein provides the further advantage of providing even better quality sound amplification by a simple, mechanical means, particularly when used in noisy environments. In order to fully realize this benefit, the chambers 33' and 35' have their ends opposite the sound pick-up head closed by walls 104 and 105. Even though the length, and thus the volume of the enclosed chambers 33' and 35' are the same, their sound resonant amplification characteristics are different because of the different location of their respective opposing pairs of side wall apertures, such side venting provides the same amplification benefit as if the tubes were cut at the position of the vent and its end allowed to remain open.

The multi-tube structure of FIGS. 1 and 2 is most simply fabricated by known plastic dip molding techniques in order to form a unitary, integral, one-piece structure. The resonant cavities 33' and 35' end at their walls 104 and 105 at the Y of the sound transmission passage 17'. This is an especially advantageous structure that is compact and simplified. The composite structure is then bendable into and out of the plane of the paper of FIG. 1. Of course, other arrangements of tubes to be utilized, such as a triangular arrangement in cross-section as done in the embodiment of FIG. 3, depending on the particular goals of the application.

Referring to FIG. 3, a different embodiment is shown wherein the sound transmission passage 17" and resonant chambers 33" and 35" correspond, respectively, to the passage 17' and chamber 33' and 35' of the structure of FIGS. 1 and 2. This embodiment illustrates that a single continuous tube 106 may be used to form both of the resonant chambers which each have different sound amplifying characteristics. In effect, the use of a single tube 106 has the ends of the resonant chambers furthest removed from the pick-up head joined together to form a single chamber. A side vent aperture 107 is provided, as well as a similar opposing aperture (not shown) in a manner as previously illustrated. This embodiment takes advantage of the fact that the portion of the resonant cavity beyond the venting apertures from the pick-up head makes no difference as to its sound amplifying characteristics. Therefore, the resonant chamber 33" has an effective length from the sound pick-up head through the common tube 106 from one end to the venting apertures 107, and the chamber 35" has a shorter effective length from the sound pick-up head through the other end of the tube 106 to the venting aperture 107. The chamber 33" is folded back on itself, thus saving space in the structure.

FIG. 3A shows a system that operates similarly to the system of FIG. 3 but which differs in its structural details. Tubes 114 and 115, forming resonant cavities 33''' and 35''', respectively, are cut before reaching the Y of the sound transmission passage 17'''. Their open ends are connected by a formed rigid tube link 116, thereby to form the cavities 33''' and 35''' into a single, connected cavity.

Yet another embodiment is illustrated with respect to FIG. 4. In this example, a commonly used Y transmission tube 108 is employed with an independent tube 109 connected (not shown) together adjacent the sound pick-up head by an appropriate manually actuated valve arrangement as described in the prior patent. In place of an open ended resonant tube that is described in the prior patent, the open end of the tube 109 is provided with a rigid plastic or metal plug 110 that is closed at its end but has a side vent adjacent thereto in the form of one pair of opposing apertures 111 and 112, and another pair of opposing apertures 113 and one not shown. As with all embodiments the side vent can take the form of one, a pair or higher number of apertures. The plug 110 is designed so their is no discontinuity in the chamber cross-sectional area; the area is preferably uniform along the entire length of the chamber.

It is thought that the use of a side vent, rather than an end vent, prevents the undesirable room noises from entering the resonant cavity because of attenuation presented by the sounds having to bend substantially 90 degrees in order to travel down the tube and enter the sound transmission passage which is connected to the users ear piece. The use of pairs of opposing apertures, as described in the specific embodiments, appears to be better than a single larger aperture, possibly because sound entering from the room through one aperture leaves through the opposite aperture without undesirably travelling down the length of the resonant cavity tube. These vents should have a total area of less than twice the cross-sectional area of the resonant cavity tube at the location of the vents in order to minimize the level of room sounds that are permitted to enter the chamber. The resonant chambers formed of the tubes and the various embodiments are otherwise completely enclosed except for the vents that are located and configured as shown. Also, the flexible tubes forming the resonant cavities most conveniently have a uniform cross-sectional area along their lengths, but this is certainly not a requirement.

Referring to FIG. 5, a sound pick-up head is shown in cross-section that is a variation of that shown in FIG. 4A of the prior patent. A flat, circular, bendable diaphragm 120 is held between frame pieces 41' and 43' to form an enclosed chamber 45' which communicates through opening 47' to the sound passages 17', 17" and 17''' of the previously described structures. A solid probe 121 is attached to the diaphragm 120 through a center hold by a clip 122. The diaphragm can be made of Mylar, or some other sheet material having a high tensile strength and the probe 121 of Nylon or some other non-breakable plastic. This structure is very rugged and resists the type of breakage that occurs with present commercial stethoscopes.

An extension 123 is provided for the probe, as shown in FIGS. 5 and 5A, which enables touching hard to reach portions of subjects, particularly with small animals. The piece 123 is hollow and opened on one end with an internal diameter such that it will snuggly fit over a short cylindrical outside surface 125 of the probe 121. The extension 123 can then be easily inserted and removed by hand without breaking the diaphragm 120.

It will be understood that the present invention is entitled to protection within the full scope of the appended claims.

I claim:

1. In a stethoscope having a sound pick-up head and at least one ear piece that are connected at opposite ends of an enclosed sound transmission passage therebetween, a sound amplifying structure comprising an elongated resonant cavity connected at one end to said enclosed sound transmission passage in the vicinity of said pick-up head, thereby allowing soundwaves from said pick-up head to simultaneously pass into both the resonant cavity and enclosed passage, a vent of said cavity to the atmosphere being provided through a side wall thereof, whereby an unvented length of said cavity from its connection with said sound transmission passage to said vent determining the range of sound frequencies detected at the pick-up head that are amplified at the ear piece.

2. The stethoscope according to claim 1 wherein said resonant cavity is completely enclosed along its length beyond said vent from its said one end, whereby interference by extraneous ambient noises surrounding the stethoscope are significantly reduced.

3. The improved stethoscope according to claim 2 wherein said resonant cavity includes a tube having characteristics similar to a tube utilized for said enclosed sound transmission passage, said tubes being integrally connected to one another.

4. The improved stethoscope according to any of claims 1, 2 or 3 wherein a cross-sectional area of said cavity is substantially uniform along its length from its connection to said sound transmission passage in said vent, said vent having a total area opening said cavity to said atmosphere that is within a range of from one-half to two times the cross-sectional area of the cavity.

5. The improved stethoscope according to any of claims 1, 2 or 3 wherein said vent comprises two apertures in the side wall of said cavity opposite each other.

6. The improved stethoscope according to any of claims 1, 2 or 3 wherein said vent comprises two apertures in the side wall of said cavity opposite each other, a total area of said apetures that vent said cavity to the atmosphere being within a range of from one-half to two times a cross-sectional area of said cavity at the position of said apetures.

7. The improved stethoscope according to claim 1 wherein said resonant cavity is formed from a flexible tube having no opening on its side but with an open end, a plug being positioned at said opened end, said plug characterized by having a closed end and forming said vents by one or more apertures in its side wall adjacent said closed end.

8. The improved stethoscope according to claim 1 wherein said cavity extends beyond said vent a distance to another end thereof, means being provided adjacent said pick-up head for selectively connecting either of said one end or said another end to said sound transmission passage as desired, the amplifying characteristics provided by connection to either of the end of the resonant cavity depending upon the distance of said vent from each of said ends.

9. The improved stethoscope according to claim 1 wherein said sound pick-up head comprises a flat diaphragm held by a shell that forms an enclosed volume behind the diaphragm that communicates with said enclosed sound transmission passage, said diaphragm carrying a a solid probe permanently attached thereto, said probe extending outward of said pick-up head on an opposite side of diaphragm than said enclosed volume, whereby the probe vibrates said diaphragm when contacting a body being examined.

10. The improved stethoscope according to claim 1 wherein said sound pick-up head comprises a diaphragm held by a shell that forms an enclosed volume behind the diaphragm that communicates with said enclosed sound transmission passage, said diaphragm carrying a probe that extends outward of said pick-up head, a probe extension being provided that frictionally engages said probe in a manner to be attached and remanned by hand, thereby to make the proble length extendable.

11. A stethoscope, comprising:
a sound pick-up head having a sound output port,
valve means for selectively opening said sound port to a first or second amplification port,
three flexible, hollow tubes integrally formed into one structure along their length between one end thereof and another end thereof, said one end of each of the three tubes being connected respectively to one of the sound port, first amplification port or second amplification port, said another end of the tube connected to the sound port being split into a Y shape, each of the other two tubes terminating in closed ends at that position, and
a vent provided through side walls of each of the two tubes connected to the first and second amplification ports in order to open the inside thereof to the atmosphere through the vent, each of the vents being positioned a different distance from said pick-up head, whereby each of the vented tubes give sound amplification of different frequency ranges when connected to receive sounds from said sound port.

12. The stethoscope according to claim 11 wherein each of said vents comprises a pair of apertures formed in the tube side walls on opposite sides thereof.

13. A stethoscope according to claim 12 wherein each of said three tubes are molded together to a common unitary structure in a single plane, thereby retaining flexibility in a direction into and out of said plane.

14. The stethoscope according to either of claims 11 or 12 wherein the total area of each tube's vent is within a range of from one-half to two times the cross-sectional area of the tube's internal cavity at the location of the vent.

* * * * *